(12) United States Patent
Lin

(10) Patent No.: US 6,824,540 B1
(45) Date of Patent: *Nov. 30, 2004

(54) APPARATUS AND METHODS FOR THE TREATMENT OF PRESBYOPIA USING FIBER-COUPLED-LASERS

(75) Inventor: J. T. Lin, Oviedo, FL (US)

(73) Assignee: SurgiLight, Inc., Orlando, FL (US)

( * ) Notice: Subject to any disclaimer, the term of this patent is extended or adjusted under 35 U.S.C. 154(b) by 168 days.

This patent is subject to a terminal disclaimer.

(21) Appl. No.: 09/706,382

(22) Filed: Nov. 6, 2000

(51) Int. Cl.⁷ .............................................. A61B 18/20
(52) U.S. Cl. ................................. 606/5; 606/4; 128/898
(58) Field of Search .............................. 606/2, 4, 5, 6, 606/10; 128/898

(56) References Cited

U.S. PATENT DOCUMENTS

| | | | | |
|---|---|---|---|---|
| 4,907,586 A | | 3/1990 | Bille et al. ..................... 606/5 |
| 5,102,409 A | * | 4/1992 | Balgorod ........................ 606/5 |
| 5,144,630 A | | 9/1992 | Lin ................................ 606/5 |
| 5,152,760 A | * | 10/1992 | Latina ............................ 606/6 |
| 5,354,331 A | | 10/1994 | Schachar ........................ 606/4 |
| 5,484,432 A | | 1/1996 | Sand .............................. 606/5 |
| 5,489,299 A | | 2/1996 | Schachar ........................ 623/4 |
| 5,520,679 A | | 5/1996 | Lin ................................ 606/5 |
| 5,529,076 A | | 6/1996 | Schachar ........................ 606/4 |
| 5,533,997 A | | 7/1996 | Ruiz .............................. 606/5 |
| 5,549,598 A | * | 8/1996 | O'Donnell, Jr. ................. 606/6 |
| 5,599,341 A | * | 2/1997 | Mathis et al. ................... 606/5 |
| 5,722,952 A | * | 3/1998 | Schachar ....................... 604/51 |
| 5,738,676 A | * | 4/1998 | Hammer et al. ................. 606/4 |
| 5,741,247 A | * | 4/1998 | Rizoiu et al. ................... 606/10 |
| 5,845,024 A | * | 12/1998 | Tsushima et al. .............. 385/33 |
| 6,156,030 A | * | 12/2000 | Neev ............................ 606/10 |
| 6,171,336 B1 | * | 1/2001 | Sawusch ..................... 623/5.11 |
| 6,197,018 B1 | * | 3/2001 | O'Donnell ....................... 606/4 |
| 6,197,056 B1 | * | 3/2001 | Schachar ..................... 623/4.1 |
| 6,203,538 B1 | * | 3/2001 | Peyman ......................... 606/5 |
| 6,258,082 B1 | * | 7/2001 | Lin ................................ 606/5 |
| 6,263,879 B1 | * | 7/2001 | Lin ................................ 606/5 |

* cited by examiner

Primary Examiner—Lee S. Cohen
(74) Attorney, Agent, or Firm—Knobbe, Martens, Olson & Bear, LLP.

(57) ABSTRACT

Systems and surgical techniques for presbyopia correction by laser removal of the sclera tissue are disclosed. The disclosed preferred embodiments of the system consists of a beam spot controller, a fiber delivery unit and a fiber tip. The basic laser including UV lasers and infrared lasers having wavelength ranges of (0.15–0.36) microns and (1.9–3.2) microns and diode lasers of about 0.98, 1.5 and 1.9 microns. Presbyopia is treated by a system which uses an ablative laser to ablate the sclera tissue outside the limbus to increase the accommodation of the ciliary body of the eye. The sclera tissue may be ablated by the laser with or without the conjunctiva layer open.

22 Claims, 3 Drawing Sheets

(A)

(B)

US 6,824,540 B1

APPARATUS AND METHODS FOR THE TREATMENT OF PRESBYOPIA USING FIBER-COUPLED-LASERS

BACKGROUND OF THE INVENTION

1. Field of the Invention

The present invention relates to methods and apparatus for the treatment of presbyopia using fiber-coupled lasers to ablate the sclera tissue.

2. Prior Art

Corneal reshaping including a procedure called photorefractive keratectomy (PRK) and a new procedure called laser assisted in situ keratomileusis, or laser intrastroma keratomileusis (LASIK) have been performed by lasers in the ultraviolet (UV) wavelength of (193–213) nm. The commercial UV refractive lasers include ArF excimer laser (at 193 nm) and other non-excimer, solid-state lasers such as those proposed by the present inventor in 1992 (U.S. Pat. No. 5,144,630) and in 1996 (U.S. Pat. No. 5,520,679). The above-described prior arts using lasers to reshape the corneal surface curvature, however, are limited to the corrections of myopia, hyperopia and astigmatism.

Refractive surgery using a scanning device and lasers in the mid-infrared (mid-IR) wavelength was first proposed by the present inventor in U.S. Pat. Nos. 5,144,630 and 5,520,679 and later proposed by Telfair et. al., in U.S. Pat. No. 5,782,822, where the generation of mid-IR wavelength of (2.5–3.2) microns were disclosed by various-methods including: the Er:YAG laser (at 2.94 microns), the Raman-shifted solid state lasers (at 2.7–3.2 microns) and the optical parametric oscillation (OPO) lasers (at 2.7–3.2 microns).

Cornmeal reshaping may also be performed by laser thermal coagulation currently conducted by a Ho:YAG laser (at about 2 microns in wavelength) proposed by Sand in U.S. Pat. No. 5,484,432. This method, however, was limited to low-diopter hyperopic corrections. Strictly speaking this prior art did not correction the true "presbyopia" and only performed the mono-vision for hyperopic patients. A thermal laser is required and the laser treated area was within the optical zone diameters of about 7 mm.

Ruiz in U.S. Pat. No. 5,533,997 proposed the use of laser ablation of cornea surface to correct presbyopic patients. This prior art, however, must generate multifocal (or bifocal) surface on the central portion of the cornea in order to achieve the desired presbyopia correction. Corneal curvature change by laser ablation in this prior art, however, did not actually resolve the intrinsic problems of presbyopic patient caused where the cornea lens loss its accommodation as a result of loss of elasticity due to age.

All the above-described prior arts are using methods to change the cornea surface curvature either by tissue ablation (such as in UV laser) or by thermal shrinkage (such as in Ho:YAG laser) and all are using lasers onto the central potion of the cornea.

The alternative method for presbyopia correction, therefore, is to increase the accommodation of the presbyopic patients by change the intrinsic properties of the sclera and ciliary tissue to increase the lens accommodation without changing the cornea curvature. This method of sclera ablation is fundamentally different from all the prior arts including that of Ruiz, in which reshaping cornea curvature into multifocal shape was required for presbyopia correction.

Correction of presbyopia via the expanding of the sclera by mechanical devices was recently proposed by Schachar in U.S. Pat. Nos. 5,489,299 and 5,354,331. These prior arts all require the implant of external band or using laser heating to affect the position of the insertion band and have the drawbacks of complexity, time consuming, costly and potential for side effects. To treat presbyopia, Schachar's other U.S. Pat. Nos. 5,529,076 and 5,722,952, proposed the use of heat or radiation on the corneal epithelium to arrest the growth of the crystalline lens by laser coagulation effects. However these two prior arts did not present any details or practical methods and there was no clinical studies have been practiced to show the effectiveness of the proposed concepts.

Roberto Albertazzi et al (Ocular Surgery News, July, 1999) recently proposed to use diamond knife for the incision of the sclera tissue outside the limbus rings to increase the space for sclera expansion. This method however caused corneal bleeding and regression is frequently found after the treatments. We note that there is intrinsic difference between a laser ablation proposed in this invention and the knife incision. The sclera space produced by the incision method is not permanent and may be greatly reduced during the tissue healing and cause the regression. This major source of regression in incision method however will not occur in the laser ablation method as proposed in this invention, where portion of the sclera tissue is permanently removed.

The "presbyopia" correction proposed by Ruitz (U.S. Pat. No. 5,533,997) using an excimer (ArF) laser also required the corneal surface to be reshaped to form "multifocal" effort for a presbyopia patents to see near and far. However, Ruitz's "presbyopia" correction is fundamentally different from that of the present patent which does not change the corneal curvature. The presbyopia correction proposed in the present patent is to increase patient's accommodation rather reshaping the cornea into "multifocal" surface.

The technique used in the prior art of Bille (U.S. Pat. No. 4,907,586) required a quasi-continuous laser having pulse duration less than 10 picoseconds and focused spot less than 10 micron diameter and the laser is confined to the interior of a selected tissue to correct myopia, hyperopia or astigmatism. Bille also proposed the laser to focused into the lens of an eye to prevent presbyopia. This prior art system is very complicate and needs a precise control of the laser beam size and focusing position. Furthermore, clinical risk of cataract may occur when laser is applied into the lens area.

Treatment of presbyopia by cold lasers was recently proposed by the present inventor in U.S. Pat. application Ser. Nos. 09/189,609 and 09/391,503. These pending patents, however, require the use of a scanning device to generate the laser ablation patterns on the cornea. These systems therefore involve with complicated hardware and software for scanning patterns and patient centration or eye movement is critical.

Accordingly, there is a strong need to treat presbyopia via laser ablation of the sclera tissue using a laser system which may be delivered by a hand held fiber unit. Furthermore, the system may be used in either non-contact or contact modes with laser beam spot sizes defined by the size and shapes of the fiber tips. System proposed in the present patent will be safer than that of prior arts because the central portion of the cornea remains intact and only the area outside the limbus will be ablated by the laser. It is yet another objective of the present patent is to provide a no-invasive method where the conjunctiva layer may be lifted to generate the "gap" for fiber tip to insert into the gap and ablate the desired patterns underneath and to avoid or minimize bleeding or infection.

SUMMARY OF THE INVENTION

The preferred embodiments of the basic surgical lasers of the present invention shall include: (a) infrared (IR) lasers having wavelengths range of about (1.4–3.2) microns including but not limited to solid state lasers of Er:glass, Ho:YAG, Er:YAG, Er:YSGG, infrared gas lasers, solid-state lasers converted by optical parametric oscillation (OPO); (b) ultraviolet (UV) lasers having wavelength range of about (190–355) nm, such as ArF (at 193 nm) and XeCl (at 308 nm) excimer lasers and solid-state lasers using frequency conversions; (c) semiconductor diode lasers at about 980 nm, (1.3–1.55) microns, and (1.8–2.1) microns; (d) diode-pumped solid state lasers having wavelength range of about (190–355) nm and (2.7–3.2) microns such as diode-pumped Er:YSGG, Er:YAG, Nd:YAG, Er:glass and Ti:saphire laser and their harmonic generation.

It is yet another preferred embodiment is to couple the basic lasers by a fiber and deliver the laser beam to the treated area of the eye by a handheld piece which is further connected to a fiber-tip at various shapes.

It is yet another preferred embodiment to focus the laser beams into a desired spot size on the treated area of the eye. Various ablation patterns may be generated manually via the fiber-connected hand piece including multiple rings of spots and radial line incisions outside the limbus.

It is yet another preferred embodimentis to open the conjunctiva layer prior to the laser ablation of the underlayer of the sclera tissue for a better control of the ablation depth and for safety reasons. It is yet another preferred embodiment is that the conjunctiva layer may be lifted to generate the "gap" for fiber tip to insert into the gap and ablate the desired patterns underneath and to avoid or minimize bleeding or infection.

Further preferred embodiments of the present invention will become apparent from the description of the invention which follows.

DETAILED DESCRIPTION OF THE INVENTION AND THE PREFERRED EMBODIMENTS

Figure 1:
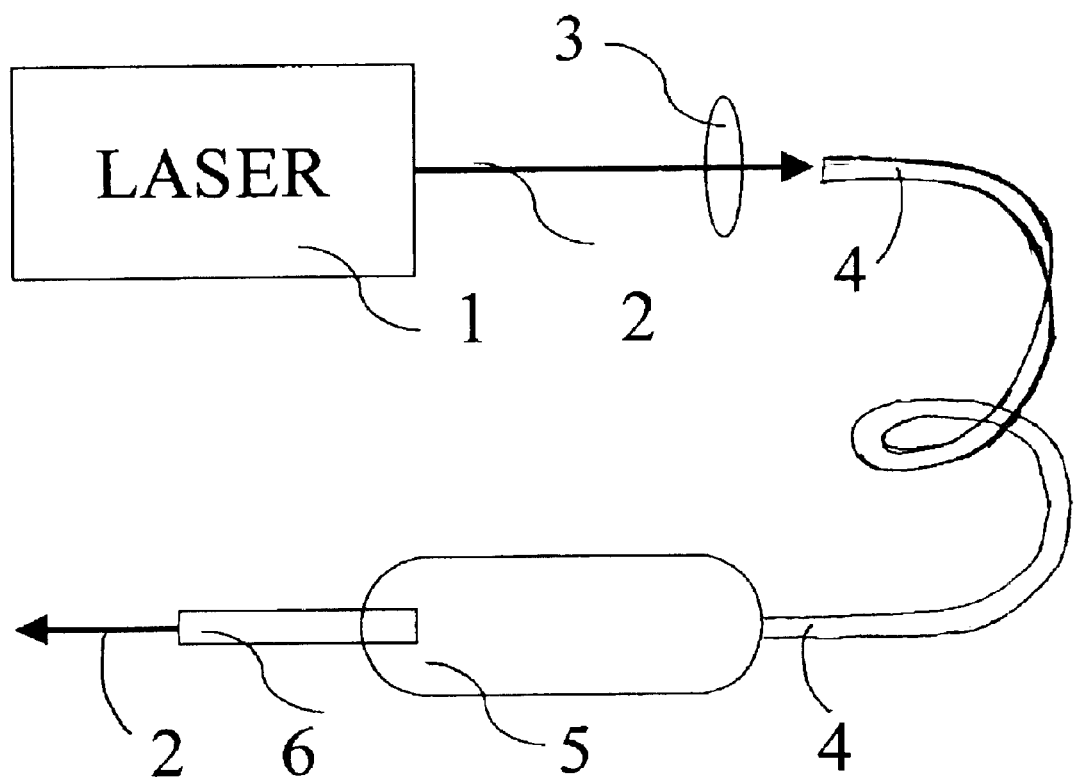
FIG. 1 is a block diagram of the integrated laser system consisting of a laser, a coupling fiber delivery unit and a hand-piece connected to a fiber-tip to control the beam spot on the treated area.

Referring to FIG. 1, a surgical laser system in accordance with the present invention comprises a basic laser 1 having wavelength 2 coupled by a focusing lens 3 to a fiber 4 which is connected to a hand-piece 5 and a fiber tip 6. The focusing lens 3, fiber 4 and fiber tip 6 are highly transparent to the wavelength 2 of the basic laser.

Still referring to FIG. 1, according to the present invention, the preferred embodiments of the basic surgical lasers for presbyopia correction procedures shall include: (a) infrared lasers having wavelengths range of about (1.4–3.2) microns including but not limited to solid state lasers of Er:glass, Ho:YAG, Er:YAG, Er:YSGG, infrared gas lasers, solid-state lasers converted by optical parametric oscillation (OPO); (b) ultraviolet (UV) lasers having wavelength range of about (190–355) nm, such as ArF (at 193 nm) and XeCl (at 308 nm) excimer lasers and solid-state lasers using harmonic generation form solid-state lasers of Nd:YAG, Nd:YLF and Alexandrite lasers frequency conversions; (c) semiconductor diode lasers at about 980 nm, (1.3–1.55) microns, and (1.8–2.1) microns; (d) diode-pumped solid state lasers having wavelength range of about (190–355) nm and (2.7–3.2) microns such as diode-pumped Er:YSGG, Er:YAG, Nd:YAG and Er:glass, and; (e) diode lasers having wavelength at about 980 nm, 1.5 microns, and 1.9 microns.

According to one aspect of the present invention, the preferable scanning laser energy per pulse on scleral surface is about (2–20) mJ in IR lasers and about (0.5–2.0) mJ in UV lasers. Focused spot size of about (0.1–0.5) mm in diameter on the corneal plane is achieved by the focusing lens 3 which consists of at least one spherical lens. The other preferred laser parameter of this invention is the laser repetition rate range of about (5–100) Hz which will provide reasonable surgical speed and minimum thermal effects. The focused beam may be scanned over the scleral surface to ablate various patterns to achieve the desired sclera expansion.

Figure 2:
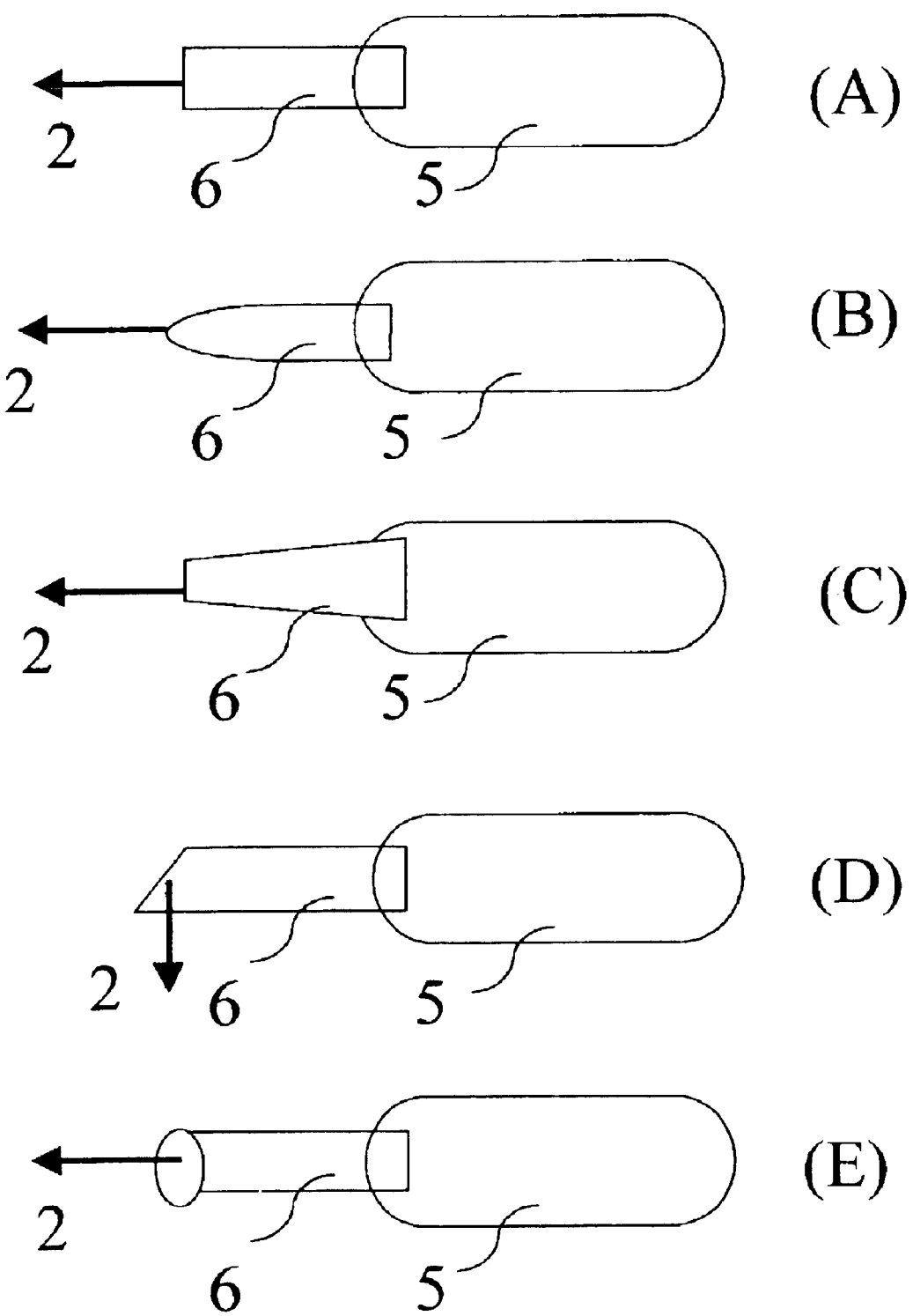
FIG. 2 shows various shapes of the fiber tips: (A) flat tip, (B) spherical tip for focused contact use, (C) conical tip, (D) 90-degree angle tip, and (E) focused slit-spot.
Figure 3:
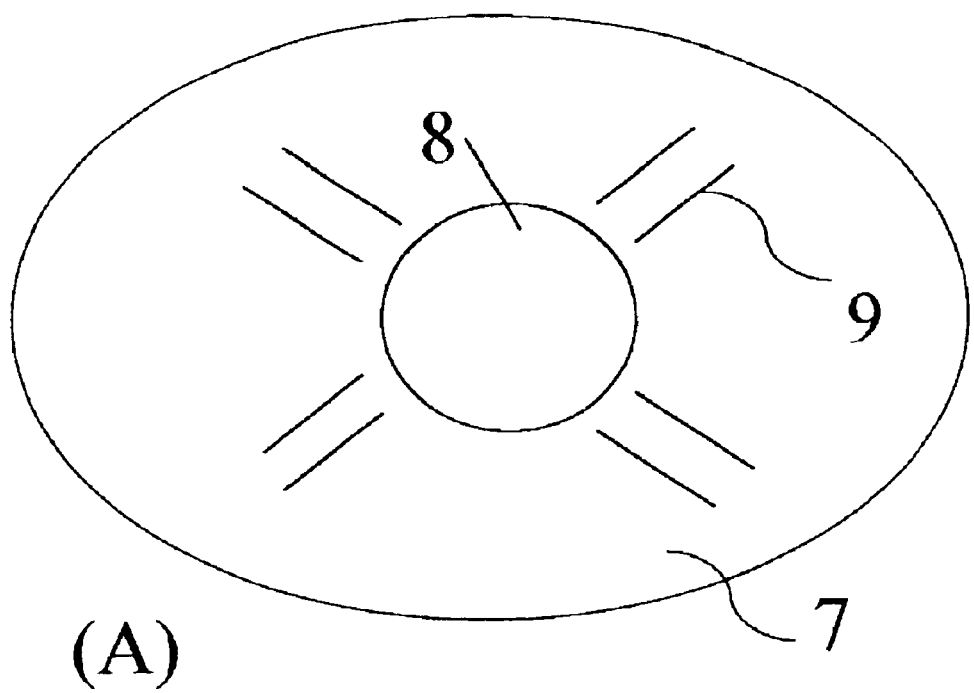
FIG. 3 shows various ablation patterns generated by the ablating laser outside the limbus.
Figure 3:
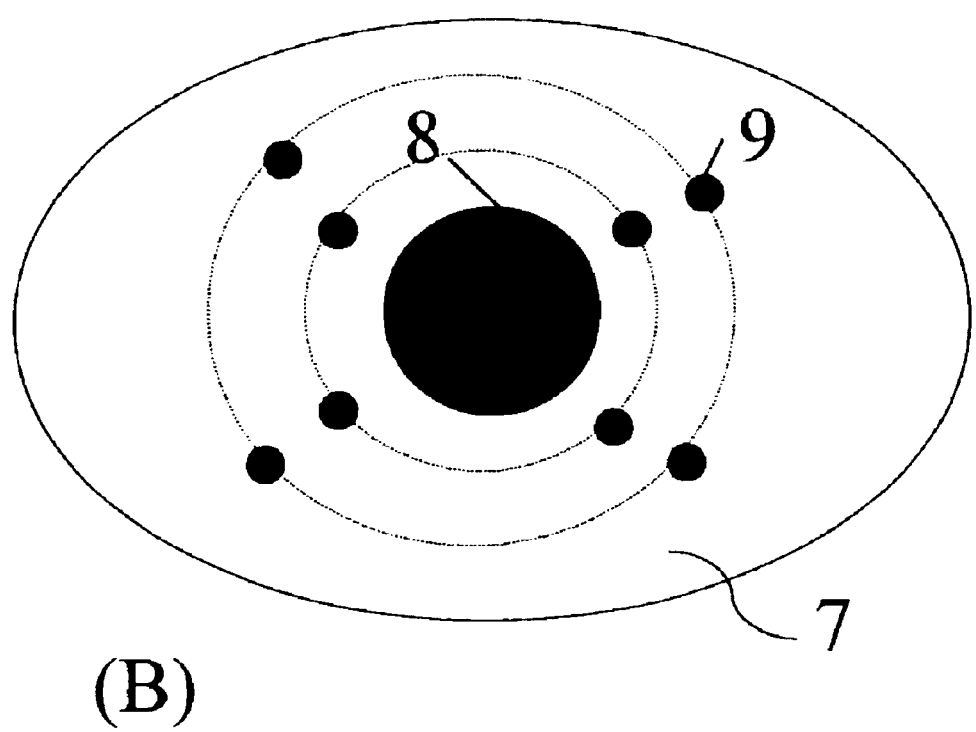

Referring to FIG. 2(A), the laser output from the fiber end having wavelength 2 is connected to the hand-piece 5 and a flat fiber tip 6 such that the output laser beam from the end of the fiber tip is a round-beam with a predetermined spot size of about (0.1.0.5) mm. FIG. 2(B) shows similar structure to FIG. 2(A), except the output round-spot beam is refocused by the spherical shape of the tip. FIG. 3 (C) shows the output beam 2 is guided by a conical shape tip such that the beam size at the end of the tip is reduced. FIG. 2(D) shows that the output beam is reflected by 90-degree by a coated fiber tip. Finally FIG. 2(E) shows an output beam spot is a slit-shape having a size of about (0.1–0.5)× (1.5–3.0) mm formed by a cylinder lens attached to the end of the fiber tip.

FIG. 3 shows an eye 7 of a presbyopic patient with ablation patterns 9 generated on the scleral area about (0.5–1.0) mm posterior to the corneal limbus 8. The preferred patterns of this invention include a ring-spot having at least one ring with at least 3 spots in each ring, and a radial-pattern having at least 3 radials. The preferred area of the ablation is defined within two circles having diameters about 10 mm and 14 mm posterior to the limbus along the radial direction of the scleral. We should note that a radial ablation pattern on the scleral surface may be generated either by an automatic scanning device or by manually scan the fiber tip by a surgeon who hold the hand piece. For the situation of the slit fiber-tip, the surgeon may easily generate the radial patterns without moving the tip.

The ablation depth of the sclera ciliary tissue is about (400–700) microns with each of the radial length of about (2.5–4.0) mm adjustable according to the optimal clinical outcomes including minimum regression and maximum accommodation for the presbyopic patients. The preferred radial ablation shall start at a distance about (4.0–5.5) mm from the corneal center and extended about (2.0–4.0) mm outside the limbus. The preferred embodiments of the radial patterns on the sclera area include at least 3 radial lines or ring-dots in a symmetric geometry as shown in FIG. 3. Still referring to FIG. 3, the preferred embodiments to generate the radial patterns on the sclera area include the following examples. (A) Scan the round laser spot of about (0.2–0.5) mm in diameter produced from the fiber tips in the radial directions to generate each of the radial lines. Generation of the radial patterns may be done either manually moving the fiber tip along the cornea radial direction or by an automatically a scanner or translator. (B) Use a focused slit-beam to generate the radial lines. In case (B), a scanning device is not needed and each of the radial lines may be generated by the slit beam directly. One preferred embodiment is to coagulate the conjunctiva layer and then cut (by a knife) a half-circle over the conjunctiva surrounding the limbus with a diameter about 10 mm which is then pushed aside in order for the ablating laser to cut the sclera layer underneath. It is also possible to use the ablating laser to cut the conjunctiva layer which however may take a longer time than cutting by a knife. Another preferred embodiment is not to open the conjunctiva layer, but to insert the fiber tip through the conjunctiva layer and ablate the sclera tissue underneath such that the procedure is done non-invasively. To do this procedure, the conjunctiva layer may be lifted to generate the "gap" for fiber tip to insert into the gap and ablate the desired patterns underneath. Additional advantages of this invasive method is to avoid or minimize bleeding or infection. We note that most of the bleeding is due to cutting of the conjunctiva tissue rather than the laser ablation of the sclera tissue. While the invention has been shown and described with reference to the preferred embodiments thereof, it will be understood by those skilled in the art that the foregoing and other changes and variations in form and detail may be made therein without departing from the spirit, scope and teaching of the invention. Accordingly, threshold and apparatus, the ophthalmic applications herein disclosed are to be considered merely as illustrative and the invention is to be limited only as set forth in the claims.

I claim:

1. A method for performing presbyopic correction in which a portion of the sclera tissue is removed by steps of:
   (a) selecting a laser having a predetermined wavelength;
   (b) selecting a beam spot controller mechanism to reduce and focus a beam produced by said laser to a fiber delivery unit;
   (c) controlling said fiber delivery unit to deliver said laser beam in a predetermined pattern onto a plurality of positions on the sclera surface to remove a portion of the sclera tissue outside the limbus area by ablating the sclera to a depth of 400–700 microns, whereby a presbyopic patient's vision is corrected to see near by increasing the accommodation of the eye.

2. A method of claim 1, wherein said laser is an ultraviolet laser having a wavelength range of about (0.15–0.36) microns and a pulse duration less than about 200 nanoseconds.

3. A method of claim 1, wherein said laser is an infrared laser having a wavelength range of about (1.4–3.2) microns.

4. A method of claim 3, wherein said infrared laser is an optically pumped Erbium:YAG laser having a wavelength of about 2.9 microns.

5. A method of claim 1, wherein said laser is an ArF excimer laser having a wavelength of 193 nm.

6. A method of claim 1, wherein said laser is a XeCl excimer laser having a wavelength of 308 nm.

7. A method of claim 1, wherein said laser is a solid state diode laser having a wavelength range of about (0.95–2.1) microns with a power higher than 2 watts and focused to a spot size less than 0.5 mm on the sclera surface.

8. A method of claim 1, in which said beam spot controller consists of at least one focusing spherical lens to couple the said laser beam to the said fiber delivery unit.

9. A method of claim 1, wherein said fiber delivery unit consists of an optical fiber having a length of about (0.5–1.5) meters and core diameter of about (0.2–0.8) mm and a hand piece connected to a fiber tip.

10. A method of claim 9, wherein said fiber delivery unit is substantially transparent to the wavelength of said laser beam.

11. A method of claim 9, wherein said fiber tip is made of a similar material as that of the fiber and is made to focus the said laser beam onto a treated sclera area of the eye, the fiber tip having a shape chosen from the group consisting of conical, spherical, 90-degree reflecting angle and flat end.

12. A method of claim 9, wherein said fiber tip focuses the said laser beam onto a treated area of the eye at a spot size of about (0.1–0.5) mm in diameter.

13. A method of claim 9, wherein said fiber tip is made in a cylinder shape to focus said laser beam onto a treated area of the eye at a line shape having a dimension of about (0.1–0.4) in width and (0.5–4.0) mm in length.

14. A method of claim 9, wherein said fiber tip is operated in a contact-mode.

15. A method of claim 9, wherein said fiber tip is operated in a non-contact mode.

16. A method of claim 1, wherein said fiber delivery unit is controlled by the surgeon to deliver the laser beam in said predetermined pattern outside the limbus by manually moving the fiber tip in the radial direction of the eye.

17. A method of claim 1, wherein said fiber delivery unit is attached to a scanning device to perform said predetermined pattern outside the limbus and scan said laser beam along the radial direction of the eye.

18. A method of claim 1, wherein said predetermined pattern outside the limbus is defined by the area between two circles having radius of about 5.0 mm and 9.0 mm, respectively.

19. A method of claim 1, wherein said predetermined pattern includes at least 3 radial lines around the area outside the limbus.

20. A method of claim 1, wherein said predetermined pattern includes at least one ring formed by 3 circular spots having a diameter of about (0.2–0.5) mm around the area outside the limbus.

21. A method of claim 1, wherein said sclera tissue is removed by said laser after the conjunctiva layer is open.

22. A method of claim 1, wherein said sclera tissue is removed by said laser without opening the conjunctiva layer.

* * * * *